United States Patent [19]

Radatus et al.

[11] Patent Number: 5,596,093
[45] Date of Patent: Jan. 21, 1997

[54] PROCESS FOR PREPARING HALOGENATED 2,3-O-CYCLOCYTIDINE DERIVATIVES

[75] Inventors: Bruno K. Radatus; Khashayar Karimian, both of Brantford; Anand Daljeet, Mississauga; Keshava Murthy, Brantford, all of Canada

[73] Assignee: ACIC (Canada) Inc., Brantsford, Canada

[21] Appl. No.: 469,506

[22] Filed: Jun. 6, 1995

Related U.S. Application Data

[60] Division of Ser. No. 191,192, Feb. 2, 1994, Pat. No. 5,527,782, which is a continuation-in-part of Ser. No. 930,605, filed as PCT/CA91/00078, Mar. 13, 1991, Pat. No. 5,399,682.

[30] Foreign Application Priority Data

Mar. 13, 1990 [CA] Canada .................................. 2012095
Mar. 13, 1990 [CA] Canada .................................. 2012096

[51] Int. Cl.$^6$ .............................. C07H 1/00; C07H 19/09
[52] U.S. Cl. ........................................ 536/55.3; 536/28.52
[58] Field of Search ................................ 536/28.52, 55.3

[56] References Cited

U.S. PATENT DOCUMENTS

| | | |
|---|---|---|
| 3,462,416 | 8/1969 | Hanze et al. .............................. 536/28.5 |
| 3,755,295 | 8/1973 | Verheyden et al. ...................... 536/28.52 |
| 3,775,397 | 11/1973 | Etzold et al. ............................ 536/28.52 |
| 3,792,040 | 2/1974 | Moffatt et al. ........................... 536/28.5 |
| 3,812,098 | 5/1974 | Moffatt et al. ........................... 536/28.5 |
| 3,899,482 | 3/1975 | Hoffer .................................... 536/28.52 |
| 4,104,461 | 8/1978 | Fox ....................................... 536/28.52 |
| 4,122,252 | 10/1978 | D'Souza et al. ......................... 536/28.52 |
| 4,124,757 | 11/1978 | Hoffer .................................... 536/28.52 |
| 4,966,891 | 10/1990 | Fujiu et al. ............................. 536/28.52 |

OTHER PUBLICATIONS

B. A. Otter et al. "Pyrimidines.XI. The conversion of 5-hydroxyuracils . . . " J. Org. Chem., vol. 36 No. 9, 1971, pp. 1251–1255.

T. Kanai et al. "Pyrimidine Nucleosides. 5, Synthesis . . . " Journal of Medicinal Chemistry, 1972, vol. 15 No. 12, pp. 1218–1221.

Zairseva et at. Chemical Abstracts, vol. 111, No. 5, Abstr #39784u, Zh. Org. Khim. 24(12): 2629–2630, 1988.

Mikhailopula et al. Chemical Abstracts, vol. 117, #1119535, 1992, Nucleosides Nucleotides, 11 (2–4): 273–8, 1992.

Agyei–Aye et al. Chemical Abstracts, vol. 112, #5650942, 1990, Nucleosides Nucleotides, 8(3): 327–37, 1989.

*Primary Examiner*—Gary L. Kunz
*Attorney, Agent, or Firm*— Nixon & Vanderhye

[57] ABSTRACT

A process from preparing 5-halogenated 2,3-O-cyclocytidine derivatives comprising reacting 2,3-O-cyclocytidine with a halogenating reagent, preferably N-bromosuccinimide, in the presence of an acid such as acetic or trifluoroacetic.

15 Claims, 1 Drawing Sheet

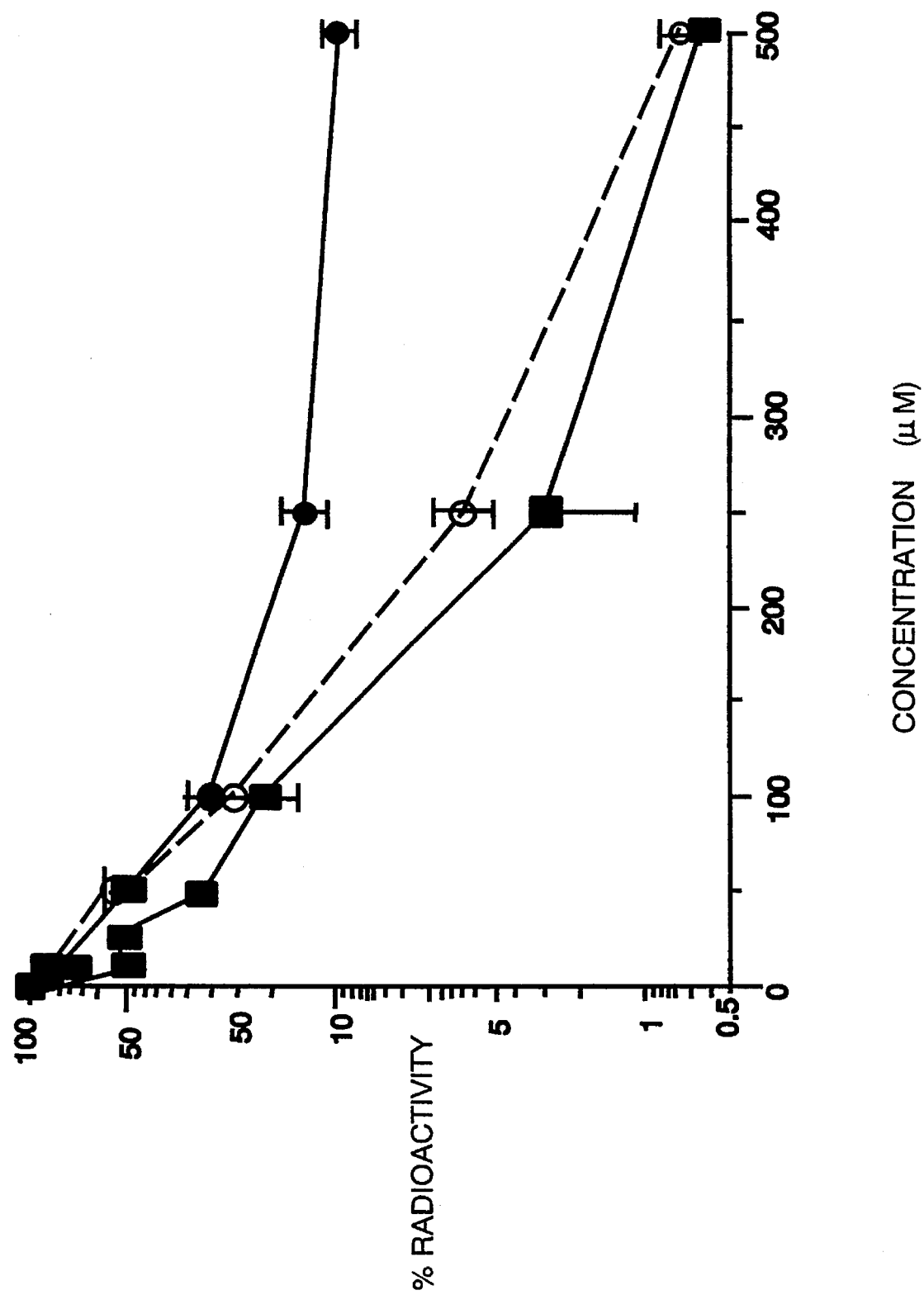

PROCESS FOR PREPARING HALOGENATED 2,3-O-CYCLOCYTIDINE DERIVATIVES

CROSS-REFERENCE TO RELATED APPLICATION

This is a Rule 60 Divisional of application Ser. No. 08/191,192, filed 2 Feb. 1994, now U.S. Pat. No. 5,527,782, which is a CIP of application Ser. No. 07/930,605, filed as PCT/CA91/00078, Mar. 13, 1991, now U.S. Pat. No. 5,399,682.

BACKGROUND OF THE INVENTION

1. Field of the Invention

The present invention relates to novel halogenated derivatives of 2,3'-O-cyclocytidine compounds and to a process for production thereof.

2. Brief Description of the Prior Art

Mizuno et al. (Tet. Lett., 4579–4584 (1965)), the contents of which are incorporated herein by reference, teach the production of 2,3'-O-cyclocytidine via a six step process which includes the production of 3'-O-mesylcytidine via a four step process from $N^4$-acetylcytidine. This corresponds to a five step process, overall, if cytidine is used as the starting material. Thus, it is not surprising that the overall yield of 3'-O-mesylcytidine produced in this manner is less than 10% (even this low yield assumes theoretical yields for two of the five steps where yield was unreported). As taught in Mizuno et al. Tet. Lett., 4579–4584 (1965)), 2,3'-O-cyclocytidine is produced from 3'-O-mesylcytidine as a crystalline freebase. Specifically, the last step in the process comprises reacting 3'-O-mesylcytidine with an excess of sodium t-butoxide to produce 2,3'-O-cyclocytidine. Unfortunately, the first step in the process involves conversion of $N^4$-acetylcytidine (NOTE: this was obtained from cytidine in only a 65% yield) to 2',5'-di-O-trityl-$N^4$-acetylcytidine in only a 20% yield. Accordingly, the process of Mizuno et al. is deficient in that it requires an onerous number of steps to produce 2,3'-O-cyclocytidine and, when produced, 2,3'-O-cyclocytidine is obtained in a relatively low yield of less than 8.5% (even this low yield assumes theoretical yields for two of the six steps where yield was unreported).

Further, Doerr et al. (J. Org. Chem., 32, 1462–1471 (1967)), the contents of which are incorporated herein by reference, found it surprising that Mizuno et al. reported isolating 2,3'-O-cyclocytidine in neutral form.

These problems of low yields of 2,3'-O-cyclocytidine has been addressed by Karimian et al. in International patent application S.N. PCT/CA91/00078 (published Sep. 19, 1991 as WO 91/13901), the contents of which are incorporated herein by reference. Specifically, Karimian et al. teach that the hydrochloride salt of 2,3'-O-cyclocytidine, Formula II,

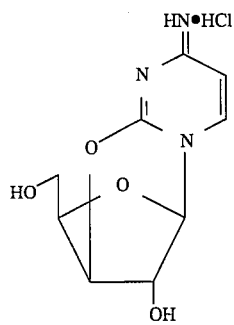

may be produced in relatively high yields by a reaction comprising the step of intramolecular rearrangement of a compound having the formula

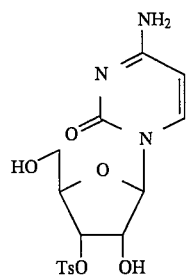

wherein Ts is a tosyl group, followed by reaction with hydrogen chloride, to produce the compound of Formula II.

As is known in the art, 2,3'-O-cyclocytidine (including its salts, analogues and derivatives) has utility as an antineoplastic and an antiviral agent.

There is an ongoing need to develop compounds related to 2,3'-O-cyclocytidine which have similar or enhanced activity as antineoplastic and antiviral agents.

SUMMARY OF THE INVENTION

It is an object of the present invention to provide novel halogenated 2,3'-O-cyclocytidine compounds.

It is another object of the present invention to provide a process for producing halogenated 2,3'-O-cyclocytidine compounds.

Accordingly, in one of its aspects, the present invention provides a compound of Formula I:

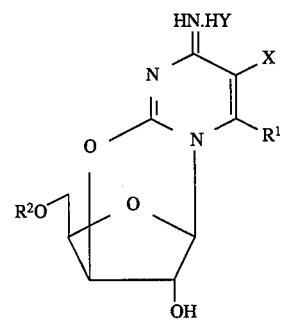

wherein:

X is a halide;

Y is selected from the group consisting essentially of halide, sulfate, acetate, tosyl, mesyl, benzoate and phosphate;

$R^1$ is selected from the group consisting essentially of hydrogen, a substituted or unsubstituted $C_1$–$C_{10}$ alkyl group and a substituted or unsubstituted $C_6$–$C_{10}$ aryl group; and $R^2$ is selected from the group consisting essentially of hydrogen, trityl, acetyl, benzyl, benzoyl, dimethoxy trityl, tosyl, mesyl and an acyl radical of an organic carboxylic acid

in which R is selected from the group consisting essentially of a substituted or unsubstituted $C_1$–$C_{20}$ alkyl group, a substituted or unsubstituted $C_6$–$C_{10}$ aryl group, a substituted or unsubstituted $C_4$–$C_{10}$ cycloalkyl group, a substituted or unsubstituted $C_7$–$C_{12}$ aralkyl group and a substituted or unsubstituted $C_7$–$C_{20}$ cage-type hydrocarbon group.

In another of its aspects, the present invention provides a process for producing a compound of Formula I:

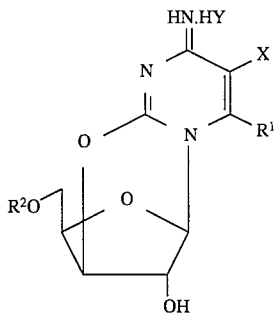

wherein:
X is a halide;
Y is selected from the group consisting essentially of halide, sulfate and acetate;
$R^1$ is selected from the group consisting essentially of hydrogen, a substituted or unsubstituted $C_1$–$C_{10}$ alkyl group and a substituted or unsubstituted $C_6$–$C_{10}$ aryl group; and
$R^2$ is selected from the group consisting essentially of hydrogen, trityl, acetyl, benzyl, benzoyl, dimethoxy trityl, tosyl, mesyl and an acyl radical of an organic carboxylic acid

in which R is selected from the group consisting essentially of a substituted or unsubstituted $C_1$–$C_{20}$ alkyl group, a substituted or unsubstituted $C_6$–$C_{10}$ aryl group, a substituted or unsubstituted $C_4$–$C_{10}$ cycloalkyl group, a substituted or unsubstituted $C_7$–$C_{12}$ aralkyl group and a substituted or unsubstituted $C_7$–$C_{20}$ cage-type hydrocarbon group, the process comprising the step of reacting a compound of Formula II:

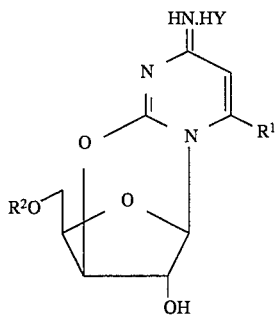

with a halogenating compound comprising X.

BRIEF DESCRIPTION OF THE FIGURE

Embodiments of the invention will be described with reference to the attached FIGURE which is a graphical illustration of % Radioactivity vs. Concentration (μM) for various compounds.

DESCRIPTION OF THE PREFERRED EMBODIMENTS

The present inventors have discovered that halogenated derivatives of 2,3'-O-cyclocytidine compounds (i.e. the compounds of Formula I) have a surprising and unexpected superior activity compared to their nonhalogenated analogues (i.e. the compounds of Formula II).

In the compounds of Formula I

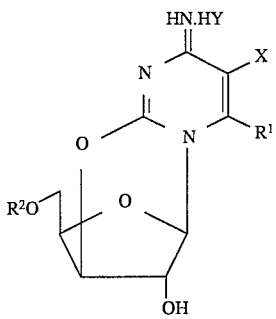

X is a halide and Y is selected from the group consisting essentially of halide, sulfate and acetate. Thus, when both X and Y are halide, they may be independently selected from the group comprising chloride, bromide, fluoride and iodide. Preferably, X is chloride or bromide, more preferably bromide. Preferably, Y is chloride.

The group $R^1$ is selected from hydrogen, a substituted or unsubstituted $C_1$–$C_{10}$ alkyl group and a substituted or unsubstituted $C_6$–$C_{10}$ aryl group. Preferably, $R^1$ is selected from the group consisting essentially of hydrogen, methyl, ethyl, propyl, isopropyl, n-butyl and t-butyl, benzyl, phenyl. Most preferably, $R^1$ is hydrogen.

The group $R^2$ is selected from the group consisting essentially of hydrogen, trityl, acetyl, benzyl, benzoyl, dimethoxy trityl, tosyl, mesyl and an acyl radical of an organic carboxylic acid

in which R is selected from the group consisting essentially of a substituted or unsubstituted $C_1$–$C_{20}$ alkyl group, a substituted or unsubstituted $C_6$–$C_{10}$ aryl group, a substituted or unsubstituted $C_4$–$C_{10}$ cycloalkyl group, a substituted or unsubstituted $C_7$–$C_{12}$ aralkyl group and a substituted or unsubstituted $C_7$–$C_{20}$ cage-type hydrocarbon group.

Preferably, the $C_1$–$C_{20}$ alkyl group is selected from the group consisting essentially of methyl, ethyl, propyl, isopropyl, n-butyl and t-butyl. Preferably, the $C_6$–$C_{10}$ aryl group is selected from the group benzyl, phenyl, tolyl and xylyl. Non-limiting examples of suitable cage-type hydrocarbon group may be found in U.S. Pat. No. 4,118,484 (Wechter et al.), the contents of which are incorporated herein by reference. The preferred choice for $R^2$ is hydrogen.

The term "substituted" as used in reference to various hydrocarbons of $R^1$ and $R^2$, is meant to encompass such groups substituted by one or more members selected from the group comprising halide, hydroxyl, carboxyl ($C_1$–$C_{10}$), nitro, alkoxy ($C_1$–$C_{10}$) and mercapto substituents.

The compounds of Formula I may be produced by reacting a compound of Formula II:

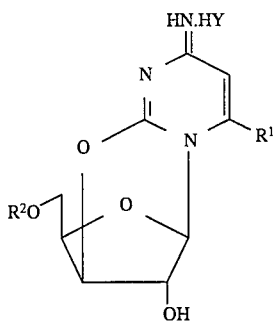

with a halogenating compound comprising X. As used throughout this specification, the term "halogenating compound" means a compound or compounds which, when reacted with a compound of Formula II will result in transfer of a halide (X) to form a compound of Formula I. The choice of halogenating compound is within the purview of a person skilled in the art and will depend on considerations such as the choice of halide (X), the conditions under which the reaction will be conducted and the like—see, for example, Volume 24 of STUDIES IN ORGANIC CHEMISTRY, entitled "The Organic Chemistry of Nucleic Acids" by Yoshihisa Mizuno, pgs. 124–133, the contents of which are incorporated herein by reference.

When X and Y are chloride, and $R^1$ and $R^2$ are hydrogen, the compound of Formula I is 5-chloro-2,3'-O-cyclocytidine hydrochloride. In this embodiment of the invention, it is preferred to prepare the compound of Formula I by reacting 2,3'-O-cyclocytidine hydrochloride with a halogenating compound such as N-chlorosuccinimide in an acidic medium. The reaction can be carried out in an aqueous or non-aqueous acidic medium, preferably a non-aqueous acidic medium. Non-limiting examples of suitable acidic media include acetic acid, trifluoroacetic acid and mixtures thereof. The preferred acidic medium is trifluoroacetic acid. Also, protic solvents such as alcohols can be used as co-solvents. An alternative approach is to react 2,3'-O-cyclocytidine hydrochloride in an acidic medium with chlorine dissolved in a suitable solvent (e.g. carbon tetrachloride). The crude product may then be worked up and recrystallized using conventional techniques.

When X is bromide, Y is chloride and R is hydrogen, the compound of Formula I is 5-bromo-2,3'-O-cyclocytidine hydrochloride. In this embodiment of the invention, it is preferred to prepare the compound of Formula I by reacting 2,3'-O-cyclocytidine hydrochloride with a halogenating compound such as N-bromosuccinimide or 1,3-dibromo-5,5-dimethyl hydantoin in an acidic medium. The reaction can be carried out in an aqueous or non-aqueous acidic medium, preferably a non-aqueous acidic medium. Non-limiting examples of suitable acidic media include acetic acid, trifluoroacetic acid and mixtures thereof. The preferred acidic medium is trifluoroacetic acid. Also, protic solvents such as alcohols can be used as co-solvents. An alternative approach is to react 2,3'-O-cyclocytidine hydrochloride in an acidic medium with bromine dissolved in a suitable solvent. The crude product may then be worked up and recrystallized using conventional techniques. The solvent is preferably a mixture of water and protic or non-protic polar solvents. Non-limiting examples of such a solvent include methanol, ethanol, isopropanol, pyridine, dimethyl formamide, acetonitrile, acetone and mixtures thereof.

When X is fluoride, Y is chloride, and $R^1$ and $R^2$ are hydrogen, the compound of Formula I is 5-fluoro-2,3'-O-cyclocytidine hydrochloride. In this embodiment of the invention, it is preferred to prepare the compound of Formula I by reacting 2,3'-O-cyclocytidine hydrochloride with a halogenating compound such as trifluoromethyl hypofluorite, cesium fluoroxysulfate, fluorine, N-fluoro-O-benzenedisulfonimide and mixtures thereof in an inert solvent. The crude product may then be worked up and recrystallized using conventional techniques.

When X is iodide, Y is chloride, and $R^1$ and $R^2$ are hydrogen, the compound of Formula I is 5-iodo-2,3'-O-cyclocytidine hydrochloride. In this embodiment of the invention, it is preferred to prepare the compound of Formula I by reacting 2,3'-O-cyclocytidine hydrochloride with a halogenating compound such as N-iodosuccinimide or iodine in an acidic medium. Non-limiting examples of suitable acidic medium include acetic acid, trifluoroacetic acid and mixtures thereof. The preferred aqueous acidic medium is trifluoroacetic acid. The crude product may then be worked up and recrystallized using conventional techniques.

Preferably, Y in Formulae I and II is chloride. It will be appreciated by those of skill in the art that Y in Formula II may be ion exchanged prior to reaction with the halogenating compound comprising X. Alternatively, it will be appreciated by those of skill in the art that Y in Formula I may be ion exchanged after the production thereof.

The compounds of Formula I have utility as antineoplastic and antiviral agents. Accordingly, the novel compounds may be formulated into pharmaceutical compositions for this purpose in a conventional manner within the purview of a person skilled in the art. Thus, the pharmaceutical compositions comprising at least one of the compounds of Formula I may adapted for administration by accepted methods of administration including oral and parenteral means. Such oral compositions may take the form of solutions, suspensions, tablets, pills, capsules, powders, sustained release formulations and the like.

The pharmaceutical composition will typically include a pharmaceutically acceptable excipient normally employed in the formation of pharmaceutical compositions intended for administration by the known routes of administration of pharmaceuticals. For example, for compositions intended for oral administration, suitable pharmaceutical excipients include the non-toxic pharmaceutically acceptable carriers such as starch, glucose, lactose, dextrose, sucrose, mannitol, sorbitol, gelatin, malt, rice, flour, chalk, silica gel, magnesium carbonate, magnesium stearate, sodium stearate, glyceryl, monostearate, sodium chloride, talc, dried skim milk, glycerol, propylene glycol, water, ethanol and the like. Mixtures of one or more of such carriers may also be used.

Aspects of the invention will be described with reference to the following Examples, which should not be considered to limit the scope of the invention.

EXAMPLE 1

Production of 5-Chloro-2,3'-O-Cyclocytidine Hydrochloride 2,3'-O-cyclocytidine hydrochloride (7.85 g; 0.03 mol) was dissolved in trifluoroacetic acid (40 mL), and thereafter, N-chlorosuccinimide (4.41 g; 0.033 mol) was added to the solution, with stirring. The reaction mixture was maintained with stirring at ambient conditions.

Periodically, an aliquot of the reaction mixture was removed and dispensed into an NMR tube and an $^1H$ NMR spectrum was obtained using a 60 MHz NMR spectrometer.

The reaction was judged complete after 70 minutes when the H-5 doublet of 2,3'-O-cyclocytidine hydrochloride substantially disappeared and the H-6 singlet of 5-chloro-2,3'-O-cyclocytidine hydrochloride appeared.

The solution was then evaporated under reduced pressure to produce a thick syrup. In a successive manner, ethanol (50 mL), water (30 mL) and ethanol (30 mL) were added to the syrup and thereafter evaporated under reduced pressure to yield 22 g of thick syrup.

Hydrochloric acid (32%; 6 g; 0.053 mol) and ethanol (30 mL) were added to the thick syrup and heated slightly to dissolve the syrup. Upon cooling, a mass of crystals was formed which were filtered and washed with ethanol. The crystals (5 g) had a melting point of 183°–185° C. and were determined to be impure by virtue of the fact that the NMR spectrum indicated a trace mount of the starting material 2,3'-O-cyclocytidine hydrochloride.

The crystals were recrystallized by: (i) dissolving in a mixture of water (4 mL) and ethanol (25 mL) with slight heating; (ii) evaporating the solution to a small volume under reduced pressure; and (iii) adding another portion of ethanol (25 mL) to induce crystallization. The crystals were gravity filtered and washed with ethanol to provide a yield of 4.0 g (45% of theoretical; 0.0135 mol) of pure 5-chloro-2,3'-O-cyclocytidine hydrochloride, which had a melting point of 190°–192° C.

The pure product was subject to elemental analysis assuming a molecular formula of $C_9H_{11}Cl_2N_3O_4$. The results of this elemental analysis are provided in Table 1.

TABLE 1

| Element | Calculated | Found |
|---|---|---|
| Carbon | 36.51 | 36.51 |
| Hydrogen | 3.74 | 3.62 |
| Nitrogen | 14.19 | 14.09 |
| Chlorine | 23.95 | 23.76 |

Using a 500 MHz NMR spectrometer, an $^1$H NMR spectrum of the pure product in DMSO-d6 was obtained. Data on peak shifts, number of peaks and coupling constants in the $^1$H NMR spectrum are reported in Table 2.

Using a 125 MHz NMR spectrometer, a $^{13}$C NMR spectrum of the pure product in DMSO-d6 was also obtained. Data on peak shifts in the $^{13}$C NMR spectrum together with the assignment of carbons are reported in Table 3.

As will be apparent from Tables 2 and 3, the data presented confirm the structure of the product to be consistent with 5-chloro-2,3'-O-cyclocytidine hydrochloride.

TABLE 2

| $^1$H NMR Spectrum (DMSO-d-6, 500 MHz) | |
|---|---|
| Shift (δ) | Assignment |
| 3.64, ABm | 2H; J4'5'$_1$=J4'5'$_2$=5.5Hz: H-5'$_1$ and H-5'$_2$ |
| 4.49, td | 1H; J3'4'=2.5Hz: H-4' |
| 4.88, d | 1H; J2'OH=3.8Hz: H-2' |
| 5.14, t | 1H; J5'$_1$OH=J5'$_2$OH=5.1Hz, exchangeable: C5'—OH |
| 5.21, bs | 1H: H-3' |
| 5.96, s | 1H: H-1' |
| 6.91, d | 1H; exchangeable: C2'—OH |
| 8.86, s | 1H: H-6 |
| 8.09 and 9.76, 2 × bs | 2H; exchangeable: NH$_2$$^+$ |

EXAMPLE 2

Production of 5-Bromo-2,3'-O-Cyclocytidine Hydrochloride (Method A)

2,3'-O-cyclocytidine hydrochloride (78.5 g; 0.3 mol) was suspended in a mixture of acetic acid (300 mL) and trifluoroacetic acid (250 mL). After 30 minutes of stirring the mixture, substantially all of the solid had dissolved.

TABLE 3

| $^{13}$C NMR Spectrum (DMSO-d-6, 125 MHz) | |
|---|---|
| Shift (δ) | Assignment |
| 58.2 | C-5' |
| 69.1 | C-3' |
| 81.5 | C-2' |
| 84.3 | C-4' |
| 90.8 | C-1' |
| 107.0 | C-5 |
| 142.6 | C-6 |
| 153.5 | C-2 |
| 162.2 | C-4 |

Bromine (57.88 g; 0.362 mol) dissolved in carbon tetrachloride (200 mL) was then added dropwise to the mixture over a period of 5½ hours. When approximately ⅓ of the bromine had been added, a precipitate had formed. The reaction was monitored by taking aliquots of the reaction mixture and running NMR spectra on same as described in Example 1.

After 24 hours, most of the precipitate had dissolved and the reaction was judged to be complete using the NMR technique described above in Example 1.

Water (300 mL) was added and resulted in the production of a two-phase reaction mixture. The two phases were separated and the top, aqueous phase was extracted with carbon tetrachloride (2×75 mL). The lower, organic phase was combined with the carbon tetrachloride extracts and extracted once with water (200 mL). The aqueous phases were combined and evaporated under reduced pressure to produce a thick syrup.

A mixture of ethanol (250 mL) and hydrochloric acid (32%; 100 mL) was added to the syrup and evaporated under reduced pressure. Ethanol (250 mL) was then added and the entire mixture was evaporated under reduced pressure to produce again a thick syrup.

Ethanol (150 mL) containing acetyl chloride (72 mL) was added to the syrup resulting in formation of a gum. The mixture was then heated to 55° C. and hydrochloric acid (32%; 25 mL) was added resulting in dissolution of the gum. Crystallization seeds were then added to the mixture. After 15 minutes of cooling, an oil appeared to form. More hydrochloric acid (32%; 55 mL) was added and the mixture was heated. Upon cooling, crystallization seeds were added to the mixture resulting in formation of crystals.

After a period of 4 hours, the crystals were filtered and washed with ethanol (3×50 mL). The washed crystals were allowed to air dry to yield 27.1 g (26.6% of theoretical; 0.0798 mol) of a first batch of crystalline product.

The mother liquor from the reaction and the wash liquids were returned to the crystallization flask (which also contained crystalline material) and stirring thereof was resumed. After 14 hours, the crystals were filtered and washed with ethanol to yield 26.16 g (25.6% of theoretical; 0.0768 mol)

of a second batch of crystalline product. Concentration of the mother liquor yielded 1.6 g of a third batch of crystalline product.

The three batches of crystalline product were combined and dissolved in a mixture of water (90 mL) and hydrochloric acid (32%; 30 mL). The resulting mixture was evaporated under reduced pressure to produce a thin syrup. Ethanol (220 mL) and crystallization seeds were then added resulting in the production of crystals. After 20 hours, the crystals were filtered, washed with ethanol (2×50 mL) and air dried to provide a yield of 42.3 g (41.4% of theoretical; 0.124 mol) of pure 5-bromo-2,3'-O-cyclocytidine hydrochloride, which had a melting point of 179°–182° C.

The pure product was subjected to elemental analysis assuming a molecular formula of $C_9H_{11}BrClN_3O_4$. The results of this elemental analysis are provided in Table 4. These results indicated that the cyclocytidine was present partially as the hydrobromide salt since the result yielded an empirical formula of $C_9H_{11}Br_{1.1}Cl_{0.9}N_3O_{3.9}$.

TABLE 4

| Element | Calculated | Found |
| --- | --- | --- |
| Carbon | 31.74 | 31.62 |
| Hydrogen | 3.26 | 3.24 |
| Nitrogen | 12.09 | 12.09 |
| Bromine | 23.46 | 25.42 |
| Chlorine | 10.41 | 9.17 |

$^1H$ and $^{13}C$ NMR spectra of the product were obtained and the data therefrom are reported in Tables 5 and 6, respectively. As will be apparent from Tables 5 and 6, the data presented confirm the structure of the product to be consistent with 5-bromo-2,3'-O-cyclocytidine hydrochloride. In this regard, it is noted that while the $^1H$ spectra for 5-chloro-2,3'-O-cyclocytidine hydrochloride and 5-bromo-2,3'-O-cyclocytidine hydrochloride are similar, the corresponding $^{13}C$ spectra distinguish the compounds from one another.

TABLE 5

$^1$H NMR Spectrum (DMSO-d-6, 500 MHz)

| Shift (δ) | Assignment |
| --- | --- |
| 3.64, ABm | 2H; J4'5'$_1$=J4'5'$_2$=5.5Hz: H-5'$_1$ and H-5'$_2$ |
| 4.49, td | 1H; J3'4'=2.5Hz: H-4' |
| 4.87, d | 1H; J2'OH=3.9Hz: H-2' |
| 5.13, m | 1H; exchangeable: C5'—OH |
| 5.21, bs | 1H: H-3' |
| 5.94, s | 1H: H-1' |
| 6.90, d | 1H; exchangeable: C2'—OH |
| 8.87, s | 1H: H-6 |
| 8.85 and 9.73, 2 × bs | 2H exchangeable: NH$_2^+$ |

TABLE 6

$^{13}$C NMR Spectrum (DMSO-d-6, 125 MHz)

| Shift (δ) | Assignment |
| --- | --- |
| 58.2 | C-5' |
| 69.1 | C-3' |
| 81.4 | C-2' |
| 84.2 | C-4' |

TABLE 6-continued $^{13}$C NMR Spectrum (DMSO-d-6, 125 MHz)

| Shift (δ) | Assignment |
| --- | --- |
| 90.7 | C-1' |
| 94.8 | C-5 |
| 145.1 | C-6 |
| 153.8 | C-2 |
| 163.0 | C-4 |

EXAMPLE 3

Production of 5-Bromo-2,3'-O-Cyclocytidine Hydrochloride (Method B)

2,3'-O-cyclocytidine hydrochloride (15.7 g; 0.06 mol) was dissolved in trifluoroacetic acid (80 mL), and thereafter, N-bromosuccinimide (11.87 g; 0.066 mol) was added to the solution, with stirring. The reaction mixture was maintained with stirring at ambient conditions.

The reaction was monitored using the NMR technique described above in Example 1 and judged to be complete after 75 minutes.

The reaction mixture was then evaporated under reduced pressure to produce a thick syrup. In a successive manner, ethanol (2×100 mL), water (50 mL) and ethanol (100 mL) were added to the syrup and thereafter evaporated under reduced pressure to yield again thick syrup.

Hydrochloric acid (32%; 12 g; 0.106 mol) and ethanol (60 mL) were added to the thick syrup and heated slightly to dissolve the syrup. Upon cooling, a mass of crystals was formed which was filtered and washed with ethanol to yield 18.38 g of product.

The crystals were recrystallized by: (i) dissolving in a mixture of water (20 mL), hydrochloric acid (32%; 10 g) and ethanol (30 mL) with slight heating; (ii) evaporating the solution under reduced pressure to produce a thin syrup; and (iii) adding a portion of hot ethanol (50 mL) to induce spontaneous crystallization. The crystals were gravity filtered and washed with ethanol to provide a yield of 17.06 g (75.9% of theoretical; 0.050 mol) of pure 5-bromo-2,3'-O-cyclocytidine hydrochloride, which had a melting point of 185°–186° C.

The pure product was subjected to elemental analysis assuming a molecular formula of $C_9H_{11}BrClN_3O_4$. The results of this elemental analysis are provided in Table 7.

TABLE 7

| Element | Calculated | Found |
| --- | --- | --- |
| Carbon | 31.74 | 31.98 |
| Hydrogen | 3.26 | 3.27 |
| Nitrogen | 12.09 | 12.27 |
| Bromine | 23.46 | 23.53 |
| Chlorine | 10.41 | 10.20 |

EXAMPLE 4

Production of 5-Iodo-2,3'-O-Cyclocytidine Hydrochloride 2,3'-O-cyclocytidine hydrochloride (7.85 g; 0.03 mol) was dissolved in trifluoroacetic acid (40 mL), and thereafter, 95% N-iodosuccinimide (7.82 g; 0.033 mol) suspended in trifluoroacetic acid (40 mL) was added to the solution, with stirring. The reaction mixture was maintained with stirring at ambient conditions and the reaction was monitored using the NMR technique described above in Example 1.

After a period of 5 hours, an oil had formed on the surface of the reaction mixture. The reaction mixture was decanted to isolate the oil which was then dissolved in acetic acid (80 mL) with warming and the two acid solutions were combined. An NMR spectrum of an aliquot of the reaction mixture indicated that the reaction was about 30% complete. After a further period of 22 hours, more 95% N-iodosuccinimide (5.2 g; 0.02 mol) was added to the mixture. After a still further period of 14 hours, more 95% N-iodosuccinimide (5.2 g; 0.02 mol) was added to the mixture. Using the NMR technique described above in Example 1, the reaction was judged complete after a further period of 4 days, notwithstanding the fact that some starting material (<10%) was present.

The reaction mixture was then evaporated to produce a thick gum (32 g). Ethanol (2×25 mL) and hydrochloric acid (32%; 2×8 g) were added and evaporated to yield a washed gum (27 g). The washed gum was dissolved in hydrochloric acid (32%; 6 g) and ethanol (30 mL), and thereafter preabsorbed on silica (40 g) and applied to a silica column (50 g). The column was initially eluted with ethyl acetate (1400 mL), which was discarded, and thereafter eluted with ethanol (800 mL). The ethanol eluate was evaporated to yield a gum.

The gum was dissolved in a mixture of hydrochloric acid (32%; 5.5 g) and ethanol (5 mL) with warming. Ethanol (25 mL) was added to the solution, heated to about 70° C. and an amount of water (2.6 mL) sufficient to clarify the solution was added.

The solution was cooled, crystallization seeds were added thereto and left stirring overnight to induce crystallization. The resulting crystals were gravity filtered and washed with ethanol (2×20 mL) to yield 4.2 g (36.1% of theoretical; 0.011 mol) of pure 5-iodo-2,3'-O-cyclocytidine hydrochloride, which had a melting point of 121.5°–124° C.

$^1$H and $^{13}$C NMR spectra of the product were obtained and the data therefrom are reported in Tables 8 and 9, respectively. As will be apparent from Tables 8 and 9, the data presented confirm the structure of the product to be consistent with 5-iodo-2,3'-O-cyclocytidine hydrochloride.

EXAMPLE 5

In Vitro Comparison Between 2,3'-O-Cyclocytidine Hydrochloride and 5-Bromo-2,3'-O-Cyclocytidine Hydrochloride In this Example, there is described an in vitro comparison between 2,3'-O-cyclocytidine hydrochloride, 5-bromo-2,3'-O-cyclocytidine hydrochloride, and 5-iodo-2,3'-O-cyclocytidine hydrochloride. The specific in vitro test involved assessing the toxicity of the compounds in a particular cell line by conducting [methyl-$^3$H]thymidine uptake experiments.

The particular cell line used in the Example was human alveolar tumour cell line A549 (hereinafter referred to as A549) obtained from The American Type Culture Collection (ATCC) as CCL 185 (lung carcinoma, human).

TABLE 8

$^1$H NMR Spectrum (DMSO-d-6, 500 MHz)

| Shift (δ) | Assignment |
|---|---|
| 3.62, ABm | 2H; J4'5'$_1$=J4'5'$_2$=5.5Hz: H-5'$_1$ and H-5'$_2$ |
| 4.47, td | 1H; J3'4'=2.5Hz: H-4' |
| 4.85, s | 1H: H-2' |
| 5.11, m | 1H: C5'—OH |
| 5.17, bs | 1H: 3' |
| 5.90, s | 1H: H-1' |
| 6.53, bs | 1H: C2'—OH |
| 8.73, s | 1H: H-6 |
| 8.43 and 9.62, 2 × bs | 2H; exchangeable: NH$_2^+$ |

Cultures were inoculated at 1×10$^5$ cells/60 mm dish, incubated for four days in the presence of various concentrations (see FIGURE) of 2,3'-O-cyclocytidine hydrochloride (o), 5-bromo-2,3'-O-cyclocytidine hydrochloride (●) and 5-iodo-2,3'-O-cyclocytidine hydrochloride (■). Thereafter, the cells were incubated with a medium supplemented with [methyl-$^3$H]thymidine (82 Ci/mmol; 5 μCi/ml) for four hours and lysed, and the amount of radioactivity incorporated into genomic DNA was measured. The IC$_{50}$ values (drug concentrations producing 50% cytotoxicity) for each compound illustrated in the FIGURE are reported in Table 10. As will be apparent from Table 10 and the FIGURE, at relatively low concentrations, 5-bromo-2,3'-O-cyclocytidine hydrochloride and 5-iodo-2,3'-O-cyclocytidine hydrochloride exhibit a significantly superior cytotoxic effect on A549 cells when compared to 2,3'-O-cyclocytidine hydrochloride.

TABLE 9

$^{13}$C NMR Spectrum (DMSO-d-6, 125 MHz)

| Shift (δ) | Assignment |
|---|---|
| 58.3 | C-5' |
| 68.8 | C-5' |
| 69.0 | C-3' |
| 81.3 | C-2' |
| 84.2 | C-4' |
| 90.5 | C-1' |
| 150.0 | C-6 |
| 154.2 | C-2 |
| 165.3 | C-4 |

EXAMPLE 6

In Vivo Comparison Between 2,3'-O-Cyclocytidine Hydrochloride, 5-Bromo-2,3'-O-cyclocytidine Hydrochloride And Other Compounds In vivo studies were conducted comparing the effectiveness of 5-bromo-2,3'-O-cyclocytidine hydrochloride (5-Br-cycloC) with one or more of 2,3'-O-cyclocytidine hydrochloride (cycloC), 1-β-D-arabinofuranosylcytosine (Ara-C), Adriamycin (ADR) and Dacarbazine (DTIC).

TABLE 10

| Compound | IC$_{50}$ (μM) |
| --- | --- |
| 2,3'-O-Cyclocytidine hydrochloride | 50 |
| 5-Bromo-2,3'-O-cyclocytidine hydrochloride | 40 |
| 5-Iodo-2,3'-O-cyclocytidine hydrochloride | 10 |

More specifically, the antitumor activity of these compounds were evaluated in two human tumor cell lines engrafted in severe combined immunodeficient (SCID) mice. The particular cell lines used in this Example were A549 (described above in Example 5) and melanoma A375 cells obtained from The American Type Culture Collection (ATCC) (hereinafter referred to as A375). Both cell lines were inoculated s.c. into SCID mice and grew progressively as tumor nodules.

The results of the in vivo study done using A375 are reported in Table 11, while the those using A549 are reported in Table 12.

With reference to Table 11, the results support the conclusion that, in treatment of A375, 5-bromo-2,3'-O-cyclocytidine hydrochloride was as effective in effecting tumor growth delay as 1-β-D-arabinofuranosylcytosine and dacarbazine, and much more effective than 2,3'-O-cyclocytidine hydrochloride. However, unlike therapy with 1-β-D-arabinofuranosylcytosine and dacarbazine, therapy with 5-bromo-2,3'-O-cyclocytidine hydrochloride resulted in no weight loss (or in two instances an actual weight gain) during therapy.

TABLE 11

| Experiment | Compound | Dose and Schedule | N (mice per group) | Growth Delay[1] (Days) | Tumor Weight[2] (% Inhibition) | Weight Loss[3] (% Decrease) | Survival Rate (%) |
| --- | --- | --- | --- | --- | --- | --- | --- |
| 1 | 5-Br-cycloC | 200 mg/kg i.p. daily × 7 | 6 | 10 | 26 | 0 | 6/6 (100) |
|   | cycloC | 1000 mg/kg i.p. daily × 7 | 6 | 2 | +6 | 0 | 6/6 (100) |
|   | Ara-C | 60 mg/kg i.p. daily × 7 | 6 | 10 | 45 | 25 | 6/6 (100) |
| 2 | 5-Br-cycloC | 250 mg/kg i.p. daily × 7 | 6 | 10 | 43 | 0 | 5/6 (83.3) |
|   | 5-Br-cycloC | 300 mg/kg i.p. × 1 | 6 | 11 | 45 | 0 | 2/6 (33.3) |
|   | Ara-C | 60 mg/kg i.p. daily × 7 | 6 | 11 | 39 | 26 | 6/6 (100) |
| 3 | 5-Br-cycloC | 250 mg/kg i.p. daily × 7 | 6 | 9 | 38 | 0 | 5/6 (83.3) |
|   | 5-Br-cycloC | 250 mg/kg i.p. every other day × 7 | 6 | 12 | 43 | +5 | 3/6[4] (50) |
|   | DTIC | 120 mg/kg i.p. every other day × 7 | 6 | 12 | 53 | 20 | 6/6 (100) |
| 4 | 5-Br-cycloC | 250 mg/kg i.p. every other day × 7 | 6 | 11 | 48 | +5 | 6/6 (100) |
|   | DTIC | 120 mg/kg i.p. every other day × 7 | 6 | 13 | 59 | 21 | 5/6 (83.3) |

[1]calculated from tumor volume curve
[2]tumor weight at day 20
[3]on the most significant day compared to phosphate buffered saline group
[4]cage flood incident resulting in fatality

TABLE 12

| Experiment | Compound | Dose and Schedule | N (mice per group) | Growth Delay[1] (Days) | Tumor Weight[2] (% Inhibition) | Weight Loss[3] (% Decrease) | Survival Rate (%) |
| --- | --- | --- | --- | --- | --- | --- | --- |
| 1 | 5-Br-cycloC | 250 mg/kg i.p. daily × 7 | 6 | 10 | 43 | 0 | 6/6 (100) |
|   | 5-Br-cycloC | 250 mg/kg i.p. every other day × 7 | 6 | 6 | 12 | +5 | 6/6 (100) |
|   | ADR | 7 mg/kg i.p. × 1 | 6 | 5 | 6 | 16 | 1/6 (16.7) |

TABLE 12-continued

| Experiment | Compound | Dose and Schedule | N (mice per group) | Growth Delay[1] (Days) | Tumor Weight[2] (% Inhibition) | Weight Loss[3] (% Decrease) | Survival Rate (%) |
|---|---|---|---|---|---|---|---|
| | Ara-C | 60 mg/kg i.p. daily × 7 | 6 | 7 | 38 | 12 | 2/6 (33.3) |
| 2 | 5-Br-cycloC | 250 mg/kg i.p. daily × 7 | 6 | 14 | 48 | 0 | 6/6 (100) |
| | ADR | 5 mg/kg i.p. × 1 | 6 | 6 | 24 | 32 | 1/6 (16.7) |
| | Ara-C | 60 mg/kg i.p. daily × 7 | 6 | 11 | 47 | 32 | 2/6 (33.3) |

[1]calculated from tumor volume curve
[2]tumor weight at day 20
[3]on the most significant day compared to phosphate buffered saline group With reference to Table 12, the results support the conclusion that 5-bromo-2,3'-O-cyclocytidine hydrochloride administered at 250 mg/kg i.p. daily×7 (MTD identified in non-tumor bearing SCID mice) significantly decreased tumor growth over a 20 day period with a growth delay of 10 days. In comparison, growth delay observed with 1-β-D-arabinofuranosylcytosine (60 mg/kg i.p. daily×7) and adriamycin (7 mg/kg i.p.×1) was 7 and 5 days, respectively. Also significant is the fact that therapy with 5-bromo-2,3'-O-cyclocytidine hydrochloride resulted in no weight loss (or an actual weight in one stance) and a survival rate of 100%. In comparision, therapy with 1-β-D-arabinofuranosylcytosine and adriamycin resulted in weight loss and a survival rate of 33.3% or less.

What is claimed is:

1. A process for producing a compound of Formula I:

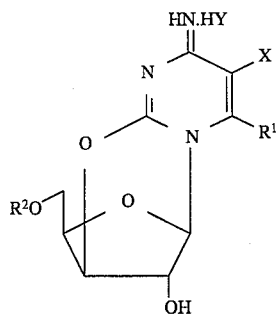

wherein:

X is a halide;

Y is selected from the group consisting of halide, sulfate and acetate;

$R^1$ is selected from the group consisting of hydrogen, $C_1$–$C_{10}$ alkyl, substituted $C_1$–$C_{10}$ alkyl, $C_6$–$C_{10}$ aryl and substituted $C_6$–$C_{10}$ aryl;

$R^2$ is selected from the group consisting of hydrogen, trityl, acetyl, benzyl, benzoyl, dimethoxytrityl, tosyl, mesyl and an acyl radical of an organic carboxylic acid

RC— in which R is selected from the group consisting of $C_1$–$C_{20}$ alkyl, substituted $C_1$–$C_{20}$ alkyl, $C_6$–$C_{10}$ aryl, substituted $C_6$–$C_{10}$ aryl, $C_4$–$C_{10}$ cycloalkyl, substituted $C_4$–$C_{10}$ cycloalkyl, $C_7$–$C_{12}$ aralkyl, substituted $C_7$–$C_{12}$ aralkyl, a $C_7$–$C_{20}$ cage-type hydrocarbon group and a $C_7$–$C_{20}$ cage-type hydrocarbon group, the process comprising the step of reacting a compound of Formula II:

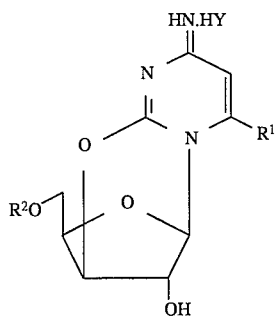

with a halogenating compound containing X.

2. The process defined in claim 1, wherein X is bromide.

3. The process defined in claim 2, wherein the compound of Formula II is initially dissolved in an acidic medium.

4. The process defined in claim 3, wherein the acidic medium is selected from the group consisting of acetic acid, trifluoroacetic acid and mixtures thereof.

5. The process defined in claim 4, wherein the halogenating compound is bromine.

6. The process defined in claim 5, wherein said bromide is initially dissolved in an organic solvent.

7. The process defined in claim 4, wherein the halogenating compound is N-bromosuccinimide.

8. The process defined in claim 1, wherein X is chloride.

9. The process defined in claim 8, wherein the compound of Formula II is initially dissolved in an acidic medium.

10. The process defined in claim 9, wherein the acidic medium is selected from the group consisting of acetic acid, trifluoroacetic acid and mixtures thereof.

11. The process defined in claim 4, wherein the halogenating compound is N-chlorosuccinimide.

12. The process defined in claim 1, wherein X is iodide.

13. The process defined in claim 12, wherein the compound of Formula II is initially dissolved in an acidic medium.

14. The process defined in claim 13, wherein the acidic medium is selected from the group consisting of acetic acid, trifluoroacetic acid and mixtures thereof.

15. The process defined in claim 14, wherein the halogenating compound is N-iodosuccinimide.

* * * * *